(12) United States Patent
Gerber

(10) Patent No.: US 7,822,482 B2
(45) Date of Patent: Oct. 26, 2010

(54) ELECTRICAL STIMULATION LEAD WITH ROUNDED ARRAY OF ELECTRODES

(75) Inventor: Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 407 days.

(21) Appl. No.: 11/194,087

(22) Filed: Jul. 29, 2005

(65) Prior Publication Data

US 2007/0027515 A1 Feb. 1, 2007

(51) Int. Cl.
*A61N 1/05* (2006.01)
(52) U.S. Cl. .................................... 607/116
(58) Field of Classification Search ............... 607/116, 607/117, 133, 134, 135, 138, 143, 148, 55–57
See application file for complete search history.

(56) References Cited

U.S. PATENT DOCUMENTS

| | | | |
|---|---|---|---|
| 5,255,678 A * | 10/1993 | Deslauriers et al. | 600/375 |
| 5,255,679 A | 10/1993 | Imran | |
| 5,265,608 A | 11/1993 | Lee et al. | |
| 5,545,219 A * | 8/1996 | Kuzma | 623/10 |
| 5,840,076 A * | 11/1998 | Swanson et al. | 606/34 |
| 5,860,974 A * | 1/1999 | Abele | 606/41 |
| 6,266,568 B1 * | 7/2001 | Mann et al. | 607/137 |
| 6,529,777 B1 * | 3/2003 | Holmstrom et al. | 607/119 |
| 6,589,238 B2 * | 7/2003 | Edwards et al. | 606/41 |
| 6,600,955 B1 | 7/2003 | Zierhofer | |
| 6,889,093 B1 | 5/2005 | Flammang | |
| 6,895,283 B2 * | 5/2005 | Erickson et al. | 607/117 |
| 7,047,084 B2 | 5/2006 | Erickson et al. | |
| 7,099,718 B1 * | 8/2006 | Thacker et al. | 607/117 |
| 7,177,702 B2 * | 2/2007 | Wallace et al. | 607/117 |
| 7,181,288 B1 | 2/2007 | Rezai et al. | |
| 7,288,096 B2 * | 10/2007 | Chin | 606/129 |
| 2002/0156513 A1 | 10/2002 | Borkan | |
| 2003/0069623 A1 | 4/2003 | Stypulkowski | |
| 2003/0093130 A1 | 5/2003 | Stypulkowski | |
| 2003/0120328 A1 | 6/2003 | Jenkins et al. | |
| 2004/0059393 A1 | 3/2004 | Policker et al. | |
| 2004/0093053 A1 | 5/2004 | Gerber et al. | |
| 2004/0111139 A1 | 6/2004 | McCreery | |
| 2005/0060014 A1 | 3/2005 | Swoyer et al. | |
| 2005/0107861 A1 | 5/2005 | Harris et al. | |
| 2005/0222632 A1 * | 10/2005 | Obino | 607/28 |
| 2005/0246004 A1 * | 11/2005 | Cameron et al. | 607/116 |

(Continued)

OTHER PUBLICATIONS

U.S. Patent Application entitled "Electrical Stimulation Lead With Conformable Array of Electrodes", U.S. Appl. No. 11/194,041, filed Jul. 29, 2005.

(Continued)

*Primary Examiner*—Scott M Getzow
*Assistant Examiner*—Amanda Patton
(74) *Attorney, Agent, or Firm*—Shumaker & Sieffert, P.A.

(57) ABSTRACT

An implantable electrical lead may include a rounded array of electrodes. The array of electrodes may be distributed across a rounded surface to position the electrodes in various positions and orientations relative to a target stimulation site. The lead may be useful in a variety of applications such as spinal cord stimulation to alleviate chronic pain, gastrointestinal stimulation to alleviate gastroparesis or obesity, pelvic floor stimulation to alleviate incontinence or sexual dysfunction, or deep brain stimulation to alleviate neurological disorders.

27 Claims, 6 Drawing Sheets

U.S. PATENT DOCUMENTS

2006/0079950 A1    4/2006   Lehnhardt et al.
2006/0241733 A1*  10/2006   Zhang et al. ................. 607/122
2006/0271137 A1   11/2006   Stanton-Hicks
2007/0027514 A1*   2/2007   Gerber ........................ 607/116

OTHER PUBLICATIONS

Office Action dated Oct. 18, 2007 for U.S. Appl. No. 11/194,041 (10 pgs.).
Responsive Amendment Jan. 18, 2008 for U.S. Appl. No. 11/194,041 (17pgs.).
Office Action dated Mar. 3, 2008 for U.S. Appl. No. 11/194,041 (12 pgs.).
Request for Continued Examination and Responsive Amendment dated Jun. 3, 2008 for U.S. Appl. No. 11/194,041 (20 pgs.).
Office Action dated Jul. 14, 2008 for U.S. Appl. No. 11/194,041 (12 pgs.).
Responsive Amendment dated Nov. 13, 2008 for U.S. Appl. No. 11/194,041 (18 pgs.).
Office Action dated Feb. 17, 2009 for U.S. Appl. No. 11/194,041 (12 pgs.).
Request for Continued Examination (RCE) and Amendment dated May 18, 2009 for U.S. Appl. No. 11/194,041 (14 pgs.).
Office Action dated Jul. 23, 2009 for U.S. Appl. No. 11/194,041 (9 pgs.).
Responsive Amendment dated Oct. 23, 2009 for U.S. Appl. No. 11/194,041 (17 pgs.).

* cited by examiner

ELECTRICAL STIMULATION LEAD WITH ROUNDED ARRAY OF ELECTRODES

TECHNICAL FIELD

The invention relates to implantable medical devices and, more particularly, leads for electrical stimulators.

BACKGROUND

Electrical stimulation is an effective therapy for a variety of conditions and diseases that adversely affect patient health. For example, electrical stimulation has been effective in alleviating chronic pain, movement disorders, gastrointestinal disorders, and pelvic floor disorders. Spinal cord stimulation systems have been found to provide relief for chronic pain. Deep brain stimulation can be effective in treatment of movement disorders such as Parkinson's disease, as well as other neurological disorders such as epilepsy. Stimulation of the gastrointestinal tract can be effective in alleviating gastroparesis and obesity. Stimulation of the pelvic floor can be effective in alleviating urinary incontinence, fecal incontinence, pelvic pain, and sexual dysfunction.

Typically, electrical stimulation is delivered by an implantable pulse generator that is chronically implanted within the patient. One or more implantable leads extending from the implantable pulse generator carry electrodes for delivery of stimulation energy to a target tissue or nerve site. A lead typically carries a set of ring electrodes. Each ring electrode extends about the circumference of the lead, and is positioned at a respective axial position along the length of the lead. In operation, different combinations of electrodes, either on a single lead or among multiple leads, can be selected for delivery of electrical stimulation energy to the patient.

The particular combinations and polarities of the electrodes may define the shape or direction of a stimulation pattern. Different combinations of electrodes may be tested to identify a configuration that provides suitable efficacy for the patient. Efficacy may be evaluated in terms of the degree of relief of symptoms of a targeted disorder, as well as severity of any side effects. The availability of multiple electrodes in the vicinity of a stimulation site increases the likelihood that an efficacious electrode combination will be identified. In addition, the electrode combination may be changed over the course of therapy to restore efficacy or explore other effective combinations. In some cases, selection of alternate electrode combinations may be necessary due to lead migration within the patient, progression of symptoms or an underlying ailment, or late onset of side effects.

SUMMARY

The invention is directed to an implantable electrical stimulation lead with a rounded array of electrodes. The array of electrodes may be distributed across a rounded surface to position the electrodes in various positions and orientations relative to a target stimulation site. The lead may be useful in a variety of applications such as spinal cord stimulation to alleviate chronic pain, gastrointestinal stimulation to alleviate gastroparesis or obesity, pelvic floor stimulation to alleviate incontinence or sexual dysfunction, or deep brain stimulation to alleviate neurological disorders.

In one embodiment, the invention provides an implantable electrical stimulation lead comprising a lead body having a proximal end and a distal end, a plurality of electrical conductors within the lead body, and a plurality of stimulation electrodes positioned at the distal end of the lead body, each of the electrodes being coupled to at least one of the conductors. The distal end of the lead body defines a rounded surface and the electrodes are positioned at various positions on the rounded surface.

In another embodiment, the invention provides an implantable electrical stimulator comprising an implantable pulse generator that generates electrical stimulation pulses, and an implantable lead coupled to the implantable pulse generator. The lead includes a lead body having a proximal end and a distal end, a plurality of electrical conductors within the lead body, and a plurality of stimulation electrodes positioned at the distal end of the lead body, each of the electrodes being coupled to at least one of the conductors. The distal end of the lead body defines a rounded surface and the electrodes are positioned at various positions on the rounded surface.

In an additional embodiment, the invention provides a method comprising applying electrical stimulation pulses to a patient via an implanted lead, wherein the lead comprises a lead body having a proximal end and a distal end, a plurality of electrical conductors within the lead body, and a plurality of stimulation electrodes positioned at the distal end of the lead body, each of the electrodes being coupled to at least one of the conductors, and wherein the distal end of the lead body defines a rounded surface and the electrodes are positioned at various positions on the rounded surface.

In various embodiments, the invention may provide one or more advantages. For example, distribution of the array of electrodes across a rounded surface may increase the spatial diversity of the electrodes. In particular, the rounded surface may provide a greater variety of distances, angles, and surface contact between the electrode array and a target stimulation site, relative to ordinary ring electrodes or paddle electrodes. Increased spatial diversity among the electrodes may increase the likelihood of obtaining an electrode combination that engages the target stimulation site in a way that supports efficacy. In some cases, the distribution of electrodes over a rounded surface may present a greater number of options for efficacious stimulation. Spatial diversity among the electrodes may be especially advantageous in applications in which deployment of a lead within a stimulation site can be difficult, such as within the sacrum.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
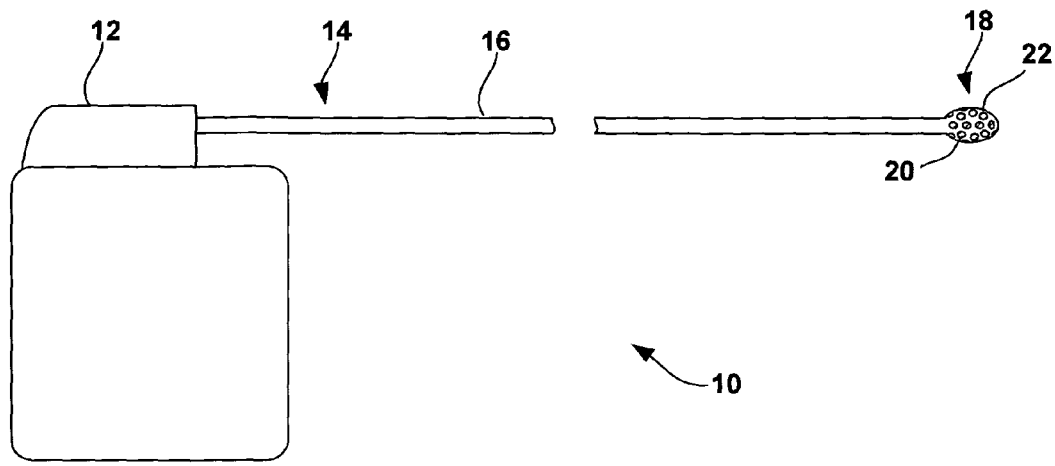
FIG. 1 is a schematic diagram illustrating an implantable electrical stimulator incorporating a pulse generator and a lead with a rounded array of electrodes.

FIG. 1 is a schematic diagram illustrating an implantable electrical stimulation system 10 incorporating a stimulator 12 and a lead with a rounded array of electrodes. As shown in FIG. 1, system 10 includes an implantable electrical stimulator 12 coupled to an implantable lead 14. Stimulator 12 may be a neurostimulator that generates neurostimulation pulses for delivery to a target stimulation site via lead 14. Stimulator 12 also may be referred to as an implantable pulse generator (IPG). In some cases, lead 14 alternatively may be used in conjunction with an external electrical stimulator, e.g., for percutaneous or trial stimulation. In either case, lead 14 may be surgically or percutaneously implanted within a patient.

Lead 14 includes a lead body 16 having a proximal end coupled to stimulator 12 and a distal end 18. Lead body 16 carries a plurality of electrical conductors (not shown in FIG. 1). A plurality of stimulation electrodes 20 are positioned at distal end 18 of lead body 16. Each of the electrodes 20 is coupled to one of the electrical conductors within lead body 16. The conductors electrically couple the electrodes to pulse generation circuitry within stimulator 12. Upon implantation, lead 14 places electrodes 20 in close proximity to a target stimulation site for delivery of stimulation pulses to the patient.

In accordance with the invention, distal end 18 of lead body 16 defines a rounded surface 22. Electrodes 20 are positioned at various positions on the rounded surface 22 defined by the distal end 18 of lead body 16. As shown in FIG. 1, distal end 18 is generally bulbous, providing a rounded surface 22 for presentation of electrodes 20. In some embodiments, the rounded surface 22 may be at least partially spherical. In other embodiments, the rounded surface 22 may be somewhat ovoid, i.e., egg-shaped. The rounded surface 22 permits electrodes 20 to be presented to tissue at the target stimulation site at a variety of different angles and orientations, providing greater spatial diversity among the electrodes.

Distribution of the array of electrodes 20 across a rounded surface 22 provides a greater variety of distances, angles, and surface contact between the electrode array and a target stimulation site, relative to ordinary ring electrodes or paddle electrodes. Rounded surface 22 also may permit a greater number of separate electrodes 20 to be provided. Increased spatial diversity among the electrodes 20 may increase the likelihood of obtaining an electrode combination that engages the target stimulation site in a way that supports efficacy. In some cases, the distribution of electrodes 20 over a rounded surface may present a greater number of options for efficacious stimulation. Spatial diversity among the electrodes 20 may be especially advantageous in applications in which deployment of a lead within a stimulation site can be difficult, such as within the sacrum.

In some embodiments, one or more electrodes 20 may be used for sensing, rather than stimulation. In particular, some electrodes 20 may be used to sense electrical potentials in a region adjacent a stimulation site. The sensed electrical potentials may be action potentials created intrinsically by the patient, either autonomously or in response to application of stimulation pulses. In this case, stimulator 12 may process the sensed electrical potentials for diagnostic purposes or for adjustment of stimulation pulses delivered to the patient. Alternatively, the sensed electrical potentials may be the potentials associated with the stimulation pulses delivered to the patient. The sensed stimulation pulse potentials may be processed to determine actual energy delivered to the patient, or in order to increase or decrease the amplitude, pulse width or pulse rate of stimulation pulses.

Figure 2:
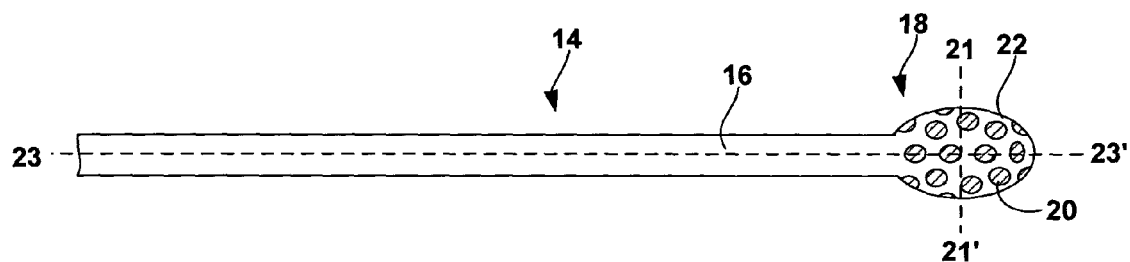
FIG. 2 is an enlarged schematic diagram illustrating the lead of FIG. 1.
Figure 3:
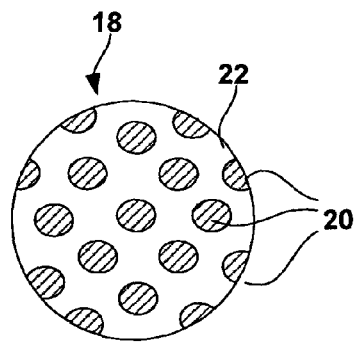
FIG. 3 is an enlarged front view of a distal portion of the lead of FIG. 2.

FIG. 2 is an enlarged schematic diagram illustrating lead 14 of FIG. 1. FIG. 3 is an enlarged front view of distal portion 18 of lead 14 of FIG. 2. As shown in FIGS. 2 and 3, electrodes 20 may be distributed across substantially the entire rounded surface 22 of distal end 18 of lead 14. For example, electrodes 20 may be positioned around an entire lateral circumference of rounded surface 22, as well as on a front, i.e., most distal, side, of rounded surface 22. Alternatively, in other embodiments, electrodes 20 may be positioned on selected portions of rounded surface 22. As illustrated in FIG. 2, electrodes 20 may be positioned at a plurality of different circumferential positions around the lateral circumference of rounded surface 22, such that at least two electrodes do not share a circumferential position. As one example, electrodes 20 may be positioned on opposing sides of the lateral circumference of rounded surface 22. In addition, electrodes 20 may be distributed in a generally regular or irregular pattern across rounded surface 22. Electrodes 20 also may have common or different sizes.

Electrodes 20 may be formed as conductive elements, such as conductive metal pads, that are formed on or within rounded surface 22. Electrodes 20 may be formed from a variety of electrically conductive, biocompatible materials. The shape of electrodes 20 may be circular, oval, rectangular, square, or irregular. Example electrode materials include platinum and platinum iridium. Electrodes 20 may be printed or otherwise deposited on rounded surface 22 at selected positions. Alternatively, electrodes 20 may be fabricated and embedded into rounded surface 22, e.g., by casting or insert molding. In either case, conductors within lead body 16 are crimped, soldered, welded, wire bonded or otherwise attached to electrodes 20 to form an electrical connection.

Distal end 18, including rounded surface 22, may be integrally formed with lead body 16, e.g., by molding, casting or the like. Alternatively, distal end 18 may be separately fabricated and attached to lead body 16, e.g., by crimping, adhesive bonding, ultrasonic welding, or the like. In general, distal end 18 and lead body 16 may be formed of biocompatible polymeric materials such as polyurethane or silicone, or a combination of such materials. In some embodiments, distal end 18 may be somewhat soft and conformable to permit the rounded surface 22, and electrodes 20, to better conform to anatomical structures within a target stimulation site.

In general, the elongated, substantially ovoid shape of distal end 18 has a diameter that increases from the proximal end toward a maximum diameter at the approximate midpoint along the length of the distal end, and increases from the distal end toward the maximum diameter at the approximate midpoint along the length of the distal end. As illustrated in FIG. 2, electrodes 20 may be positioned at various positions along the length of rounded surface 22. In this manner, electrodes 20 may be positioned at various distances from the longitudinal axis of rounded surface 22. In one embodiment, electrodes 20 are positioned on both a proximal portion (e.g., proximal to line 21-21') of rounded surface 22 and a distal portion (e.g., distal to line 21-21') of rounded surface 22. The length of rounded surface 22 may be in a range of approximately 4 to 20 mm. The maximum cross-sectional diameter of rounded surface 22 taken in a plane perpendicular to the longitudinal axis of lead body 16, i.e., along line 21-21', may be in a range of approximately 3 to 12 mm.

Although rounded surface 22 is described as substantially ovoid or "egg-like," an egg tends to have one end that is larger in diameter than the other end. Although such a shape may be used, it is more likely that the rounded surface 22 will have substantially equal diametric profiles between the proximal end and the midpoint and the distal end and the midpoint of the rounded surface. Accordingly, rounded surface 22 will tend to have a substantially oval cross-section taken along a line 23-23' of FIG. 2, i.e., in a plane taken along a longitudinal extent of distal end 18.

Figure 4:
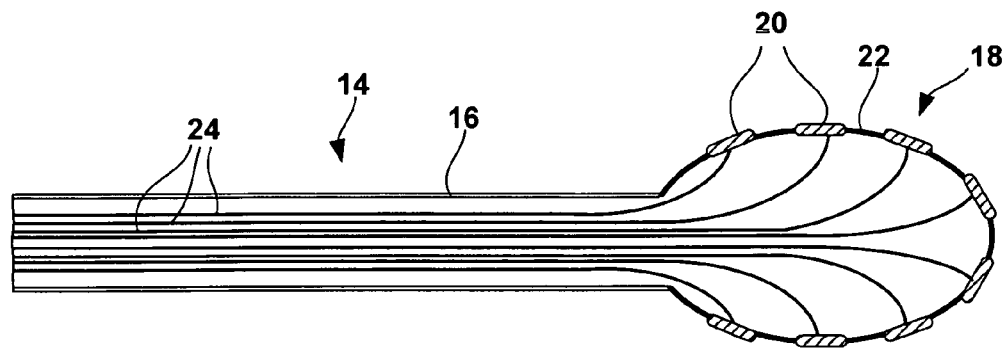
FIG. 4 is a cross-sectional side view of a lead with a rounded array of electrodes and a set of axial conductors.

FIG. 4 is a cross-sectional side view of a lead 14 with a rounded array of electrodes 20 and a set of axial conductors 24. In the example of FIG. 4, conductors 24 extend axially along the length of lead body 16. At distal end 18 of lead body 16, conductors 24 are coupled to respective electrodes 20. At a proximal end of lead body 16, conductors 24 are coupled to the output of stimulation pulse generator circuitry. Conductors 24 may be formed from any of a variety of flexible, electrically conductive materials. One example is MP35N™ alloy, which is a biocompatible, nonmagnetic, nickel-cobalt-chromium-molybdenum alloy with high strength and corrosion resistance, and a silver core to improve conductance. Lead 14 may include at least eight, at least sixteen, or at least thirty-two coiled conductors 28 and associated electrodes 20.

Figure 5:
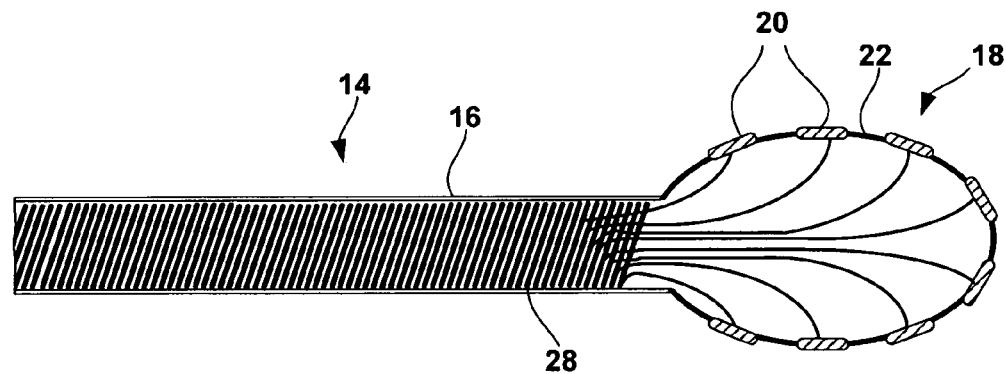
FIG. 5 is a cross-sectional side view of a lead with a rounded array of electrodes and a set of coiled conductors.

FIG. 5 is another cross-sectional side view of a lead 14 with a rounded array of electrodes and a set of coiled conductors 28. In the example of FIG. 5, coiled conductors 28 are formed as mono- or multi-filar coils. In some cases, the use of coiled conductors may provide enhanced structural integrity. Coiled conductors 28 are wound in a helical coil, e.g., at alternating turns, such that multiple conductors can be coiled together. In some embodiments, as in the example of FIG. 4, lead 14 may include at least eight, at least sixteen, or at least thirty-two coiled conductors 28 and associated electrodes 20.

Figure 6:
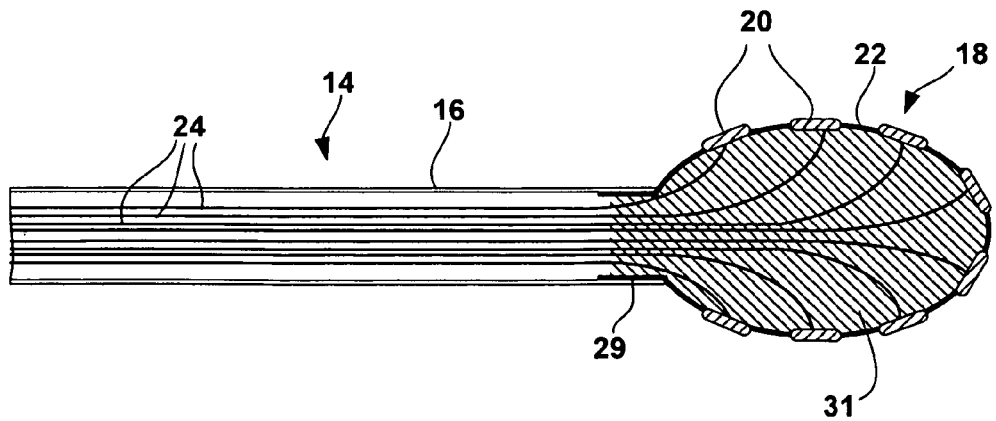
FIG. 6 is a cross-sectional side view of the lead of FIG. 4, showing a distal portion filled with an elastomeric material.

FIG. 6 is a cross-sectional side view of the lead of FIG. 4, showing a distal end 18 filled with an elastomeric material 31. In the example of FIG. 6, rounded surface 22 and electrodes 20 are arranged generally as shown in FIGS. 4 and 5. In addition, conductors 24 are configured as axial conductors, as in the example of FIG. 4, although coiled conductors may be provided. As shown in FIG. 6, an elastomeric material 31 substantially fills in interior space defined by rounded surface 22.

Elastomeric material 31 may improve the conformability of distal end 18 upon deployment within a target stimulation site. As an example, elastomeric material 31 may be silicone that is injected into the interior region of rounded surface 22 and then cured or otherwise set. In the example of FIG. 6, distal end 18 is fabricated as a separate component, with a collar 29, that is inserted into, or over, lead body 16 to couple the distal end 18 to the lead body 16. For example, collar 29 may be attached to lead body 16 by crimping, adhesive bonding, ultrasonic welding, or the like.

The number of electrodes 20 and conductors 24 or 28 may vary according to a given stimulation application. In some embodiments, lead 14 may include eight, sixteen, thirty-two or more electrodes 20 to provide a large number of independently accessible stimulation orientations within a target stimulation site. For some stimulation applications, such as spinal cord stimulation or stimulation of the sacral or pudendal nerves, distal end 18 may have a surface area in a range of approximately 30 to 200 square millimeters.

Distal end 18 may have a cross-sectional diameter, taken transverse to the longitudinal axis of lead 14, that increases from a minimum diameter at the junction between distal end 18 and lead body 16 to a maximum diameter approximately mid-length of the distal end 18, and then decreases in diameter toward the distal-most tip of the distal end 18. In this manner, distal end 18 provides a rounded surface. The maximum diameter of distal end 18, taken transverse to the longitudinal axis of leady body 16, as indicated by line 21-21' in FIG. 2, may be in a range of approximately 3 to 12 mm. Lead body 16 may have a substantially uniform outer diameter of approximately 1 to 10 mm.

Given a surface area of approximately 30 to 450 square mm, each electrode 20 may have a surface area of approximately 0.25 to 25 square mm for eight electrodes, approximately 0.25 to 15 square mm for sixteen electrodes, and approximately 0.125 to 10 square mm for thirty-two electrodes. Electrodes of the size and number described above should provide a relatively large number of independently accessible stimulation sites while leaving sufficient spacing between electrodes to avoid excessive redundancy. The above dimensions may vary according to the application envisioned for lead 14.

Lead 14 may be tunneled through patient tissue to deploy distal end 18 at a desired stimulation site. Distal end 18 and lead body 16 may accommodate a stylet to guide and steer lead 14 for implantation. A distal tip of the stylet may extend into distal end 18 to temporarily provide distal end with enhanced column strength to support tunneling. Dilators, sheaths and the like may be used for percutaneous implantation of lead 14. However, lead 14 alternatively may be surgically implanted, e.g., by an open incision.

Figure 7:
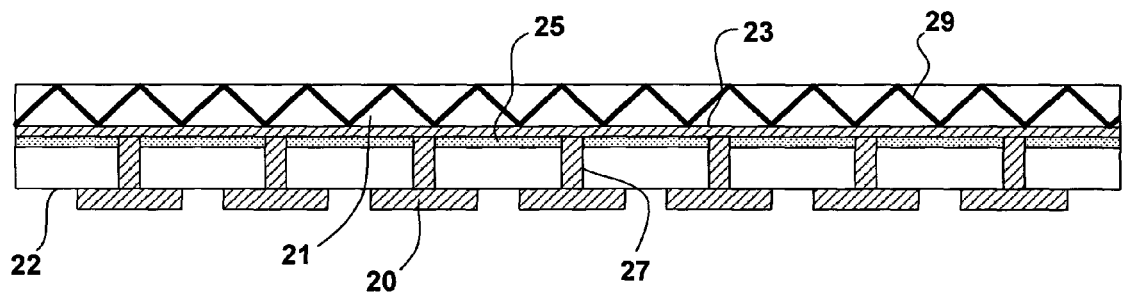
FIG. 7 is a cross-sectional side view of a multi-layer structure that may be used to form a rounded array of electrodes.
Figure 8:
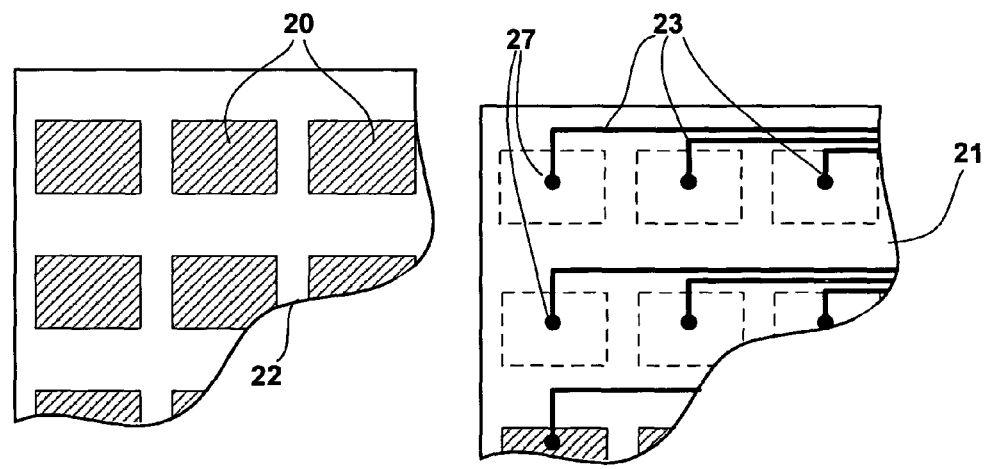
FIG. 8 is a plan view of individual layers within the multi-layer structure of FIG. 7.

FIG. 7 is a cross-sectional side view of a multi-layer structure that may be used to form a rounded array of electrodes. FIG. 8 is a plan view of individual layers within the multi-layer structure of FIG. 7. As shown in FIG. 7, the multi-layer structure may include conformable polymeric layers corresponding to rounded surface 22. Rounded surface 22 carries an array of electrodes 20, which may be printed or otherwise deposited in a desired pattern while the respective surfaces are laid out flat. Electrodes 20 may have common or different sizes and be positioned in regular or irregular patterns. Although rounded surface 22 may be laid out flat for fabrication, it is still referred to as rounded for convenience. A support layer 21 carries electrically conductive material 23. The conductive material 23 may be etched away from support layer 21 to form conductive traces. Alternatively, conductive material 23 may be printed or otherwise deposited on support layer 21 in desired patterns.

Support layer 21 may be formed from a flexible, polymeric material such as silicone or polyurethane. The multi-layer circuit may be formed in a manner similar to fabrication of a flex circuit. Additional flexible layers may be provided to enhance conformability. In some embodiments, regions between adjacent layers may be filled, e.g., by injection or coating, with an elastomeric material, such as silicone, to further enhance conformability. The elastomeric material may be cured following formation to partially harden the material, e.g., by application of heat or radiation. Alternatively, a fluid such as silicone may be allowed to remain in a semi-liquid or gel form, enhancing conformability.

The conductive material 23 carried by support layer 21 may be bonded to rounded surface 22 by an adhesive layer 25.

Conductive through-holes 27, i.e., vias, are formed to couple selected traces of conductive material 23 to selected electrodes 20 on rounded surface 20, as shown in FIGS. 7 and 8. The traces of conductive material 23 may be coupled, at a proximal edge of distal end 18, to corresponding axial or coiled conductors that extend along the length of lead body 16 for electrical connection to stimulator 12.

As further shown in FIG. 7, a supporting frame 29 may be embedded in the multi-layer stack, e.g., within support layer 21. The supporting frame 29 may be configured to bias the multi-layer stack into a desired, rounded shape upon completion of the fabrication of electrodes 20, traces of conductive material 23, and vias 27. The supporting frame 29 may be fabricated from a biocompatible metal such as titanium, stainless steel or a shape memory alloy such as Nitinol. Once the multi-layer structure of distal end 18 is released from a manufacturing jig, the supporting frame 29 causes distal end 18 to assume the desired, rounded shape. At this point, distal end 18 may be attached to lead body 16. Alternatively, additional processing may be performed, such as milling of the multi-layer structure to remove excess polymeric material. Other techniques may be sued to bias the shape of distal end 18, such as differential tensioning of particular layers within the multi-layer stack to cause a particular shape to be assumed.

Conductive traces within distal end 18 may be electrically coupled to respective conductors within lead body 16, e.g., by soldering, crimping, welding, wire bonding, or the like. Electrodes 20 may have the same size or different sizes. For example, different electrode sizes may be appropriate depending on the position of an electrode 20, the use of an electrode as stimulation or sensing electrode, or the use of the electrode as an anodic or cathodic electrode.

Figure 9:
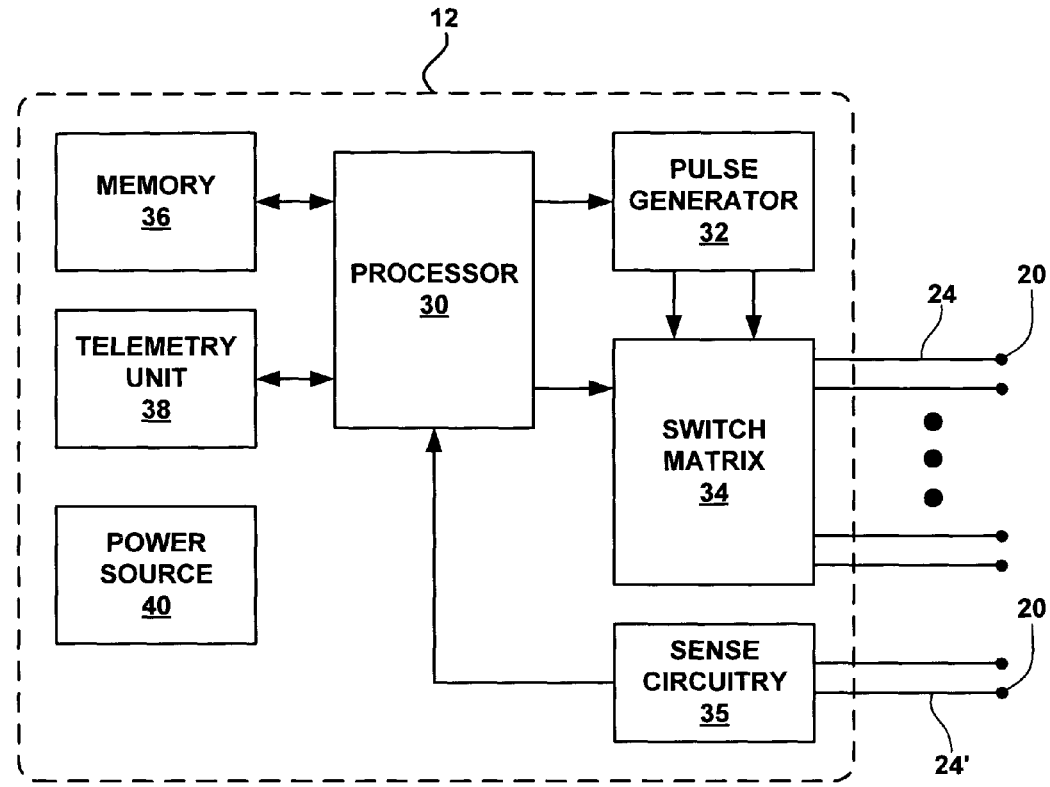
FIG. 9 is a block diagram illustrating exemplary components of an implantable electrical stimulator.

FIG. 9 is a block diagram illustrating exemplary components of an implantable electrical stimulator 12. Stimulator 12 may be used in conjunction with lead 14, as depicted in any of FIGS. 1-6. As shown in FIG. 9, stimulator 12 may include a processor 30, pulse generator 32, switch matrix 34, sense circuitry 35, memory 36, telemetry unit 38, and power source 40. Stimulator 12 has a biocompatible housing, e.g., of titanium or stainless steel. Pulse generator 32 generates electrical stimulation pulses at an amplitude (voltage or current), pulse width and pulse rate determined by processor 30. Sense circuitry 35 is optional, and processes sensed electrical potentials obtained by a subset of the electrodes 20 carried by lead 14.

The amplitude, pulse width and pulse rate parameters of stimulation pulses delivered by pulse generator 32 are selected to address any of a variety of symptoms or disorders. For example, pulse generator 32 may produce stimulation pulses with parameters selected to alleviate chronic pain, gastrointestinal disorders such as gastroparesis or obesity, and pelvic floor disorders such as incontinence, sexual dysfunction or pain. Accordingly, the stimulation pulses may be applied to the spinal cord, gastrointestinal tract, sacral nerves or pudendal nerves. The stimulation pulses alternatively may be applied to peripheral nerve stimulation. The pulses also may be used in conjunction with the lead described herein to provide deep brain stimulation for alleviation of movement disorders such as Parkinson's disease, as well as other neurological disorders such as epilepsy.

An exemplary range of neurostimulation stimulation pulse parameters likely to be effective in alleviating symptoms of one or more of chronic pain, a gastrointestinal disorder, a urinary tract disorder such as incontinence, sexual dysfunction, or peripheral nerve stimulation, are as follows:

1. Frequency: between approximately 0.5 Hz and 500 Hz, more preferably between approximately 5 Hz and 250 Hz, and still more preferably between approximately 10 Hz and 50 Hz.
2. Amplitude: between approximately 0.1 volts and 50 volts, more preferably between approximately 0.5 volts and 20 volts, and still more preferably between approximately 1 volt and 10 volts.
3. Pulse Width: between about 10 microseconds and 5000 microseconds, more preferably between approximately 62 microseconds and 620 microseconds, and still more preferably between approximately 180 microseconds and 450 microseconds.

Switch matrix 34 applies stimulation pulses generated by pulse generator 32 across selected electrodes 20 within a lead 14, or within two or more leads. The stimulation pulses may be applied in a bipolar or multipolar arrangement, in which multiple electrodes 20 are selected for delivery of stimulation pulses, e.g., across or among different electrode pairs or groups. Alternatively, in some cases, stimulation pulses may be applied in a unipolar arrangement, in which stimulation pulses are applied between a single electrode 20 selected from the electrodes 20, and a reference electrode carried by the housing of stimulator 12.

Processor 30 specifies electrode combinations and respective electrode polarities. Stimulation pulses may be applied across two electrodes 20, as anode and cathode, or across multiple electrodes with different electrodes designated as anodes and cathodes. In response to electrode combinations and polarities specified by processor 30, switch matrix 34 applies the stimulation pulses to the appropriate electrodes 20 via conductors 24. As an alternative to switch matrix 34, in some embodiments, stimulator 12 may include multiple pulse generators 32, each coupled to a given electrode or across a given electrode pair.

Memory 36 stores instructions for execution by processor 30 to control pulse generator 32 and switch matrix 34. For example, memory 36 may store programs defining different sets of stimulation parameters and electrode combinations. Memory 36 also may store operational information relating to operation of stimulator 12. Memory 36 may include any form of computer-readable media such as random access memory (RAM), read only memory (ROM), electronically programmable memory (EPROM or EEPROM), or flash memory, or any combination thereof. Processor 30 may be realized by one or more microprocessors, digital signal processors (DSPs), Application-Specific Integrated Circuits (ASIC), Field-Programmable Gate Arrays (FPGA), or other equivalent integrated or discrete logic circuitry.

Telemetry unit 38 supports wireless communication between stimulator 12 and an external programmer. Processor 30 controls telemetry unit 38 to receive programming information and send operational information. Programming information may be received from an external clinician programmer or an external patient programmer. Wireless telemetry may be accomplished by radio frequency (RF) communication or proximal inductive interaction of with a programmer.

Power source 40 delivers operating power to the components of stimulator 12. Power source 40 may include a rechargeable or nonrechargeable battery and a power generation circuit to produce the operating power. In some embodiments, battery recharging may be accomplished through proximal inductive interaction between an external charger and an inductive charging coil within stimulator 12. In other embodiments, operating power may be derived by transcutaneous inductive power generation, e.g., without a battery.

Sense circuitry 35 may be provided, in some embodiments, to process electrical potentials sensed by a subset of the electrodes 20. In particular, some electrodes 20 may be used to sense electrical potentials in a region adjacent a stimulation site, either for diagnostic purposes or closed loop control of stimulation pulse parameters. Electrical potentials may be sensed across two or more sense electrodes, or between one electrode carried by lead 14 and a reference electrode carried by a housing associated with stimulator 12. The electrical potentials obtained by sense circuitry 35 may be stored in memory 36. With sense circuitry 35, lead 14 may include both stimulation electrodes and sense electrodes.

Figure 10:
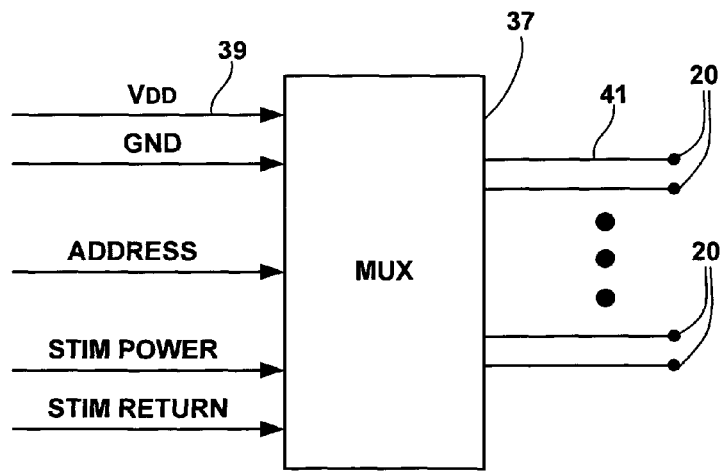
FIG. 10 is a block diagram illustrating a multiplexer (MUX) arrangement for use with a lead as described herein.

FIG. 10 is a block diagram illustrating a multiplexer (MUX) arrangement for use with a lead as described herein. In some embodiments, a lead body 16 may include a multiplexer (MUX) chip 37 adjacent distal end 18 of lead 14. In this case, lead body 16 may contain a set of input conductors 39 that extend from a proximal end of lead 14 to the MUX chip 37, and a set of output conductors 41 that extend from the MUX to respective electrodes 20. The number of output conductors 41 corresponds to the number of electrodes 20, as there is one output conductor for each electrode 20. However, the number of output conductors 41 is greater than the number of input conductors 39. The use of a MUX chip 37 within lead body 16 can reduce the number of input conductors 39 that must extend along the entire length of the lead body.

With the multiplexer placed near distal end 18, the number of input conductors 39 that must extend along substantially the entire length of lead body 16 can be reduced. For example, the input conductors 39 may include a chip power conductor VDD, a chip ground conductor GND, a serial addressing conductor ADDRESS, a stimulation power conductor STIM POWER, and a stimulation return conductor STIM return. The chip power and chip ground conductors VDD, GND deliver operating power to MUX chip 37. The stimulation power and return conductors deliver stimulation pulses for application across a set of electrodes 20 in distal end 18 of lead 14. The serial addressing conductor carries a serial codeword that identifies a combination of electrodes for application of stimulation pulses. In response to the codeword, MUX chip 37 configures a switch matrix to direct the stimulation pulses across the specified combination of two or more electrodes. The codeword may be transmitted by pulse width modulation or other serial bus schemes, and may specify the electrodes to be included in an electrode combination, as well as the polarities of the electrodes. In response to the address codeword, MUX chip 37 applies the stimulation current across the specified set of electrodes.

Figure 11:
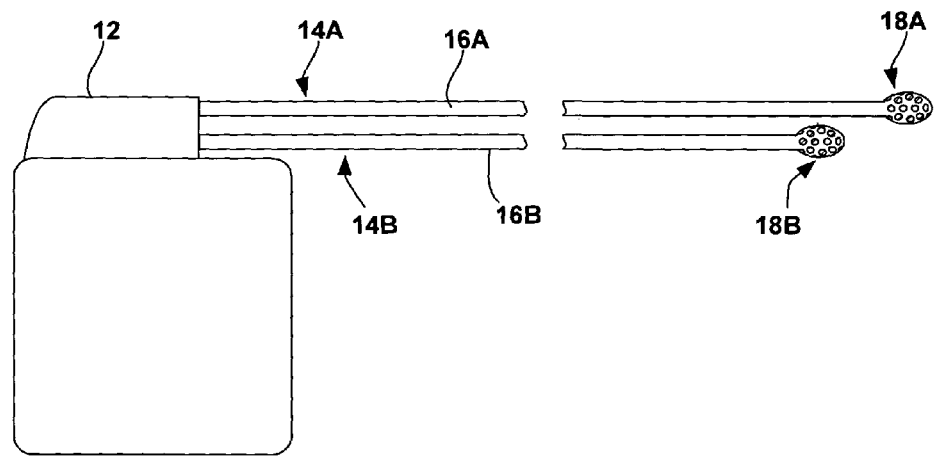
FIG. 11 is a schematic diagram of an implantable electrical stimulator with two leads with rounded arrays of electrodes.

FIG. 11 is a schematic diagram of an implantable electrical stimulator 12 with two leads 14A, 14B having lead bodies 16A, 16B with rounded arrays of electrodes at respective distal ends 18A, 18B. In the example of FIG. 11, stimulation pulses can be applied between not only electrodes in an electrode array carried by a single lead 14A, but also between electrodes carried by different leads 14A, 14B. The application of stimulation pulses between electrodes on different leads 14A, 14B may further enhance the variety of spatial stimulation sites available for delivery of stimulation pulses. The use of two leads 14A, 14B may be especially useful in spinal cord stimulation (SCS) applications in which each lead extends along a respective side of the spinal cord.

Figure 12:
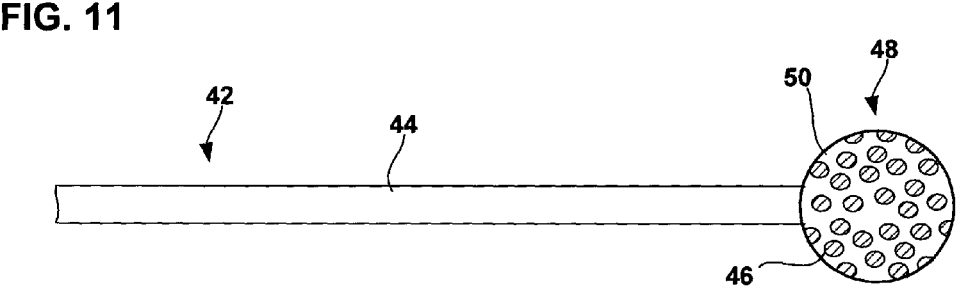
FIG. 12 is a schematic diagram of an implantable lead with a substantially spherical array of electrodes.

FIG. 12 is a schematic diagram of an implantable lead 42 having a lead body 44 with a substantially spherical array of electrodes 46 at a distal end 48. Lead 42 may substantially conform to the various embodiments of lead 14 described herein. In the example of FIG. 12, electrodes 46 are distributed over a rounded surface 50, as is the case with lead 14 depicted in FIGS. 1-6, but the rounded surface is more spherically shaped. Other shapes or arrangements, such as hemispherical or partially spherical electrode arrays, are also possible.

Figure 13:
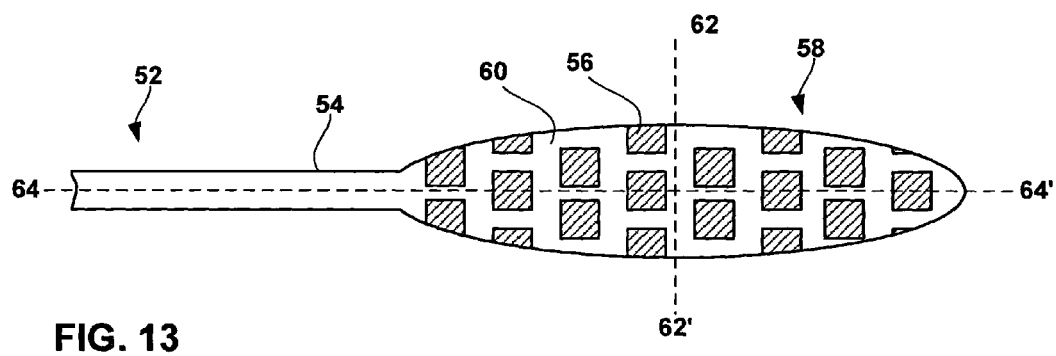
FIG. 13 is a schematic diagram of an implantable lead with an elongated, substantially ovoid array of electrodes.

FIG. 13 is a schematic diagram of an implantable lead 52 having a lead body 54 with an elongated, substantially ovoid array of electrodes 56 at a distal end 58. The elongated, substantially ovoid shape of distal end 58 provides a rounded surface 60 over which electrodes 56 are distributed. In the example of FIG. 13, electrodes 56 are distributed in a series of circumferential rows. However, other regular or irregular patterns of electrodes are possible. In general, the elongated, substantially ovoid shape of distal end 58 has a diameter that increases from the proximal end toward a maximum diameter at the approximate midpoint along the length of the distal end, and increases from the distal end toward the maximum diameter at the approximate midpoint along the length of the distal end.

The length of rounded surface 60 may be in a range of approximately 4 to 20 mm. The maximum cross-sectional diameter of rounded surface 60, taken in a plane perpendicular to the longitudinal axis of lead body 54, i.e., along line 62-62', may be in a range of approximately 3 to 12 mm. Although rounded surface 60 is described as substantially ovoid or "egg-like," an egg tends to have one end that is larger in diameter than the other end. Although such a shape may be used, it is more likely that the rounded surface 60 will have substantially equal diametric profiles between the proximal end and the midpoint and the distal end and the midpoint of the rounded surface. Accordingly, rounded surface 60 will tend to have a substantially oval cross-section taken along a line 64-64' of FIG. 13, i.e., along a plane taken along a longitudinal axis of the rounded surface.

Figure 14:
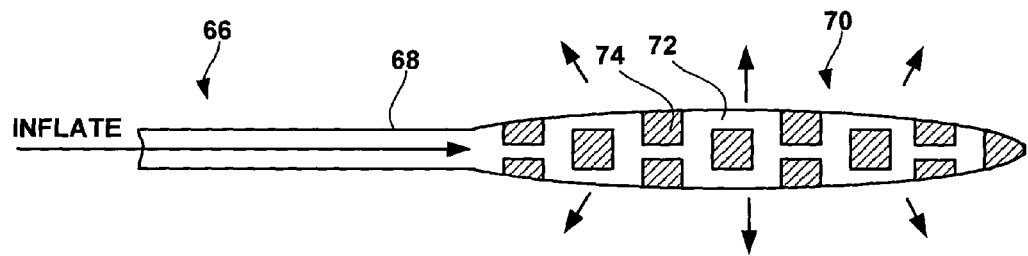
FIG. 14 is a schematic diagram of an implantable lead with an inflatable array of electrodes in a deflated state.
Figure 15:
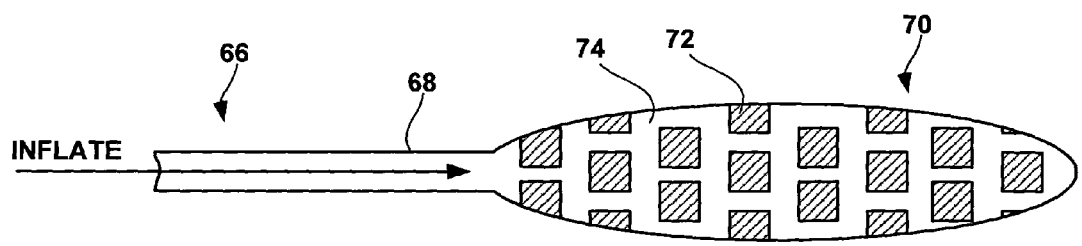
FIG. 15 is a schematic diagram of an implantable lead with an inflatable array of electrodes in an inflated state.

FIGS. 14 and 15 are schematic diagram of an implantable lead 66 with an inflatable, balloon-like array of electrodes. FIG. 14 shows lead 66 in a deflated state, while FIG. 15 shows lead 66 in an inflated state. In the example of FIGS. 14 and 15, lead 66 includes a lead body 68 with a distal end 70 having a rounded surface 72 over which an array of electrodes 74 is formed. The rounded surface 72 is formed from a flexible, biocompatible material, such as silicone or polyurethane. Lead body 68 defines an inner lumen that serves as an inflation channel for transmission of an inflation fluid into an interior area of distal end 70. Upon expansion, the spacing between electrodes 74 is increased. In addition, the expanded diameter of distal end 70 may assist in anchoring the array of electrodes 74 relative to a target stimulation site.

Once lead 66 is placed within a patient, a physician applies the inflation fluid and then closes the inflation channel to maintain the fluid pressure within distal end 70. The inflation channel may be closed, e.g., with a small pin or clamp. The physician then couples the various conductors (not shown in FIGS. 11 and 12) carried by lead body 68 to appropriate contacts within a stimulator 12 (not shown in FIGS. 11 and 12). The conductors and electrodes 74 may be insulated from the inflation fluid to prevent electrical shorting. Alternatively, the inflation fluid may be substantially non-conductive of electrical energy.

If explanation is required, the physician may open the inflation channel to withdraw the inflation fluid from distal end 70, facilitating removal of the lead. The inflation fluid, which may be a liquid, gas, or gel, expands distal end 70 and rounded surface 72. Examples of suitable inflation fluids include saline or sterile water. In some embodiments, a radio-opaque marker may be included in distal end 70 or in the inflation fluid. In some embodiments, the inflation fluid may be curable, e.g., by heat or radiation, to solidify. However, solidified materials may make non-surgical explanation more difficult than when fluid or semi-fluid materials are used.

Various embodiments of the described invention, including stimulator 12, may include processors that are realized by microprocessors, Application-Specific Integrated Circuits (ASIC), Field-Programmable Gate Arrays (FPGA), or other equivalent integrated or discrete logic circuitry. The processor may also utilize several different types of data storage media to store computer-readable instructions for device operation. These memory and storage media types may include any form of computer-readable media such as magnetic or optical tape or disks, solid state volatile or non-volatile memory, including random access memory (RAM), read only memory (ROM), electronically programmable memory (EPROM or EEPROM), or flash memory. Each storage option may be chosen depending on the embodiment of the invention.

Many embodiments of the invention have been described. Various modifications may be made without departing from the scope of the claims. For example, although the invention has been generally described in conjunction with implantable neurostimulation devices, it may also be used with other implantable medical devices, such as electrical muscle stimulation devices, and functional electrical stimulation (FES) devices. These and other embodiments are within the scope of the following claims.

The invention claimed is:

1. An implantable electrical stimulator comprising:
   an implantable pulse generator that generates electrical stimulation pulses; and
   an implantable lead coupled to the implantable pulse generator, the lead including a lead body having a proximal end and a distal end, a plurality of electrical conductors within the lead body, and a plurality of stimulation electrodes positioned at the distal end of the lead body, each of the electrodes being coupled to at least one of the conductors, wherein the distal end of the lead body defines a rounded surface, the rounded surface comprising a proximal portion in which a radius increases and a distal portion in which the radius decreases in a direction toward the distal end of the lead body, and the electrodes are positioned at various positions on the proximal portion and the distal portion of the rounded surface and at a plurality of different circumferential positions around a lateral circumference of the rounded surface, and wherein the implantable pulse generator is configured to apply a stimulation pulse to a selected subset of the plurality of the electrodes positioned on the rounded surface.

2. The stimulator of claim 1, wherein the rounded surface is at least partially spherically-shaped.

3. The stimulator of claim 1, wherein the rounded surface is at least partially ovoid.

4. The stimulator of claim 1, wherein the rounded surface has a radius that varies along a longitudinal axis of the lead body to define a curvature.

5. The stimulator of claim 1, wherein the rounded surface has a substantially oval-shaped cross-section in a plane taken along a longitudinal axis of the rounded surface.

6. The stimulator of claim 1, wherein the stimulation electrodes include at least eight stimulation electrodes.

7. The stimulator of claim 1, wherein the stimulation electrodes include at least sixteen stimulation electrodes.

8. The stimulator of claim 1, wherein the lead is a first lead, the stimulator further comprising a second lead coupled to the pulse generator, the second lead being configured similarly to the first lead.

9. The stimulator of claim 1, wherein the electrodes comprise conductive pads formed on the rounded surface.

10. The stimulator of claim 1, wherein the pulse generator generates neurostimulation pulses having parameters selected to alleviate symptoms of one or more of chronic pain, a gastrointestinal disorder, a urinary tract disorder, or sexual dysfunction.

11. The stimulator of claim 1, further comprising one or more sensing electrodes positioned at the distal end of the lead body.

12. The stimulator of claim 1, wherein the rounded surface is at least partially inflatable.

13. The stimulator of claim 1, wherein the plurality of different circumferential positions comprises opposing sides of the lateral circumference of the rounded surface.

14. The stimulator of claim 1, wherein at least some electrodes of the plurality of stimulation electrodes are distributed in one or more circumferential rows, each of the circumferential rows including two or more electrodes.

15. The stimulator of claim 1, wherein the distal end of the lead body comprises a multiplexer chip, the conductors are electrically coupled to the multiplexer chip, and the multiplexer chip directs the stimulation pulse to the selected subset of the plurality of the electrodes positioned on the rounded surface.

16. The stimulator of claim 1, wherein the implantable pulse generator comprises a switch matrix that applies the stimulation pulse to the selected subset of the plurality of the electrodes.

17. A method comprising applying electrical stimulation pulses to a patient via an implanted lead, wherein the lead comprises a lead body having a proximal end and a distal end, a plurality of electrical conductors within the lead body, and a plurality of stimulation electrodes positioned at the distal end of the lead body, each of the electrodes being coupled to at least one of the conductors, and wherein the distal end of the lead body defines a rounded surface, the rounded surface comprising a proximal portion in which a radius increases and a distal portion in which the radius decreases in a direction toward the distal end of the lead body, and the electrodes are positioned at various positions on the proximal portion and the distal portion of the rounded surface and at a plurality of different circumferential positions around a lateral circumference of the rounded surface, and wherein applying the electrical stimulation pulses comprises applying the electrical stimulation pulses to a selected subset of the plurality of the electrodes positioned on the rounded surface.

18. The method of claim 17, further comprising positioning the distal end of the lead body proximate a target nerve site within the patient.

19. The method of claim 18, further comprising selecting the target nerve site and parameters of the electrical stimulation pulses to alleviate symptoms of one or more of chronic pain, a gastrointestinal disorder, a urinary tract disorder, or sexual dysfunction.

20. The method of claim 17, wherein the rounded surface has a radius that varies along a longitudinal axis of the lead body to define a curvature.

21. The method of claim 17, wherein the stimulation electrodes include at least sixteen stimulation electrodes.

22. The method of claim 17, wherein the lead includes one or more sensing electrodes, the method further comprising sensing an electrical potential via the sensing electrodes.

23. The method of claim 17, wherein the rounded surface is at least partially inflatable, the method further comprising inflating the rounded surface upon deployment of the distal end of the lead within the patient.

24. The method of claim 17, wherein the plurality of different circumferential positions comprises opposing sides of the lateral circumference of the rounded surface.

25. The method of claim 17, wherein at least some electrodes of the plurality of stimulation electrodes are distributed in one or more circumferential rows, each of the circumferential rows including two or more electrodes.

26. The method of claim 17, wherein the distal end of the lead body comprises a multiplexer chip, the conductors are coupled to the multiplexer chip, and wherein applying the electrical stimulation pulses to the selected subset of the plurality of electrodes comprises directing the stimulation pulse to the selected subset of the plurality of the electrodes via the multiplexer chip.

27. The method of claim 17, wherein the lead is coupled to an implantable pulse generator that comprises a switch matrix, and wherein applying the electrical stimulation pulses to the selected subset of the plurality of the electrodes comprises applying the electrical stimulation pulses to the selected subset of the plurality of the electrodes via the switch matrix of the implantable pulse generator.

* * * * *